United States Patent [19]

Sam

[11] 4,189,611
[45] Feb. 19, 1980

[54] ORTHO-NITROPHENYLETHYLENE GLYCOLS

[75] Inventor: Donnie J. Sam, Wilmington, Del.

[73] Assignee: E. I. Du Pont de Nemours and Company, Wilmington, Del.

[21] Appl. No.: 913,905

[22] Filed: Jun. 8, 1978

Related U.S. Application Data

[62] Division of Ser. No. 700,968, Jun. 29, 1976, Pat. No. 4,111,960, which is a division of Ser. No. 545,603, Jan. 30, 1975, Pat. No. 3,991,033.

[51] Int. Cl.² .................... C07C 31/14; G03C 1/68
[52] U.S. Cl. .................... 525/472; 430/281; 430/270; 430/302; 430/307; 568/705
[58] Field of Search ......................................... 568/705

[56] References Cited

U.S. PATENT DOCUMENTS

3,849,137  11/1974  Barzynski et al. ............... 96/67

OTHER PUBLICATIONS

Hébert et al., "Can. J. Chem.", 52(1), pp. 187–189 (1974).
Yagupolskii et al., "J. Gen. Chem. USSR", 30, pp. 1314–1317 (1960).
Wubbels et al., "Tetrahedron Letters", 20, pp. 1689–1691 (1970).
Shirai et al., "J. Appl. Poly. Sci.", 17, pp. 1617–1619 (1973).
Leggetter et al., "Can. J. Chem.", 42, pp. 990–1004 (1964).
Baumgarten et al., "J. Am. Chem. Soc.", 80, pp. 1977–1981 (1958).
Barton et al., "J.C.S. Chem. Comm.", pp. 432–433 (1975).
Yagupolskii et al., "Zhur. Obsh. Khim., " 28 Nr. 6, pp. 1608–1610 (1958).

*Primary Examiner*—Joseph E. Evans

[57] ABSTRACT

Substituted dioxolanes are provided having the formula

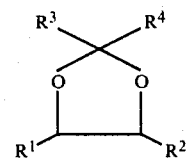

wherein $R^1$ and $R^2$ are H or a phenyl group substituted with up to 5 substituents of lower alkyl or nitro, with the proviso that at least one of $R^1$ and $R^2$ is a phenyl group having an orthonitro substituent; and $R^3$ and $R^4$ are each H or lower alkyl. These dioxolanes, as well as appropriate dioxanes, are used to intercalate a polyoxymethylene polymer to make such a polymer having thermally stable but photochemically sensitive and degradable random linkages

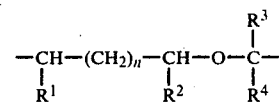

in the chain where n is 0 or 1, $R^3$ and $R^4$ are H or lower alkyl and at least one of $R^1$ and $R^2$ is a phenyl group with an orthonitro substituent. By exposing a film of the polymer to light through a transparency followed by heating or a heated treatment with base, a relief image of the copy on the transparency is obtained.

3 Claims, No Drawings

ORTHO-NITROPHENYLETHYLENE GLYCOLS

RELATIONSHIP TO OTHER APPLICATIONS

This application is a divisional of copending application Ser. No. 700,968, now U.S. Pat. No. 4,111,960 filed June 29, 1976 which in turn is a division of applicaton Ser. No. 545,603, filed Jan. 30, 1975, now U.S. Pat. No. 3,991,033.

BACKGROUND OF THE INVENTION

1. Field of the Invention

This invention relates to polyoxymethylene polymers containing random thermal and base stable but photochemically degradable groups and to methods of relief imaging using the same.

2. The Prior Art

Lithographic printing plates and photoresists having a photosensitive polymer working layer containing o-nitrocarbinol ester groups have been described in U.S. Pat. No. 3,849,137 issued Nov. 19, 1974. These polymers differ structurally from those of the present invention.

Hèbert et al., Can. J. Chem. 52(1) 187 (1974) have described o-nitrophenylethylene glycol and some dioxolanes made therewith which are intermediates described and claimed in the instant invention.

3. SUMMARY OF THE INVENTION

The polymers of the present invention are random copolymers containing polyoxymethylene chains with interspersed photosensitive units, wherein both ends are joined to oxygen, said units having the formula

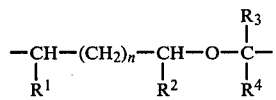

wherein $R^1$ and $R^2$ are H or phenyl optionally substituted with up to 5 substituents of lower alkyl, preferably methyl, or $-NO_2$, n is 0 or 1, $R^3$ and $R^4$ are H or lower alkyl, preferably H or methyl, with the provisos (i) that at least one of $R^1$ and $R^2$ is a phenyl group having at least one orthonitro substituent, (ii) that when n is 1, either both $R^1$ and $R^2$ are o-nitrophenyl groups or one of $R^1$ and $R^2$ is H, said photosensitive units being present in an amount of from 0.001 to 0.05, preferably 0.002 to 0.01 units per $-CH_2O-$ units, said polymers having a number average molecular weight of from 1000 to 100,000, and preferably having an inherent viscosity of 0.7 to 1.5 measured in hexafluoroisopropanol (HFIP) in 0.5% concentration at 30° C., which corresponds to a number average molecular weight for polymers of this type of about 15,000 to about 40,000.

The novel polymers of this invention are made by intercalation of preformed polyoxymethylene polymers with substituted dioxolanes, where n=o, and with substituted dioxanes, where n=1, of the formulae:

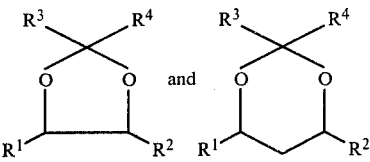

In these formulae $R^1$, $R^2$, $R^3$ and $R^4$ are as defined above. Dioxolanes are more readily obtained and are preferred.

Because the above ring structures can cleave to form the intercalated units in two ways where $R^1$ is not the same as $R^2$, two structures are possible and probably occur in such instances, where $R^1$ and $R^2$ are interchanged. When $R^3$ and $R^4$ are each H, the intercalated unit derived from the cyclic compounds includes a $-CH_2O-$ unit, indistinguishable from the chain units derived from the poloxyoxymethylene so that regardless of the difference between $R^1$ and $R^2$ no ambiguity occurs when the group is included in the chain, although such ambiguity will persist when the intercalated unit is an end group. End groups possible from dioxalanes are thus:

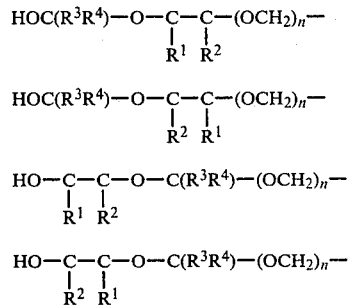

likewise four possible end groups can occur with the dioxanes. In the above end groups the terminal hemiacetal group can be removed, together with possible $-(CH_2O)_nH$ ends in the intercalated polymer by preliminary heat treatment alone or in the presence of a base. Further, if the initial polymers contain thermally stable end groups such as acetate groups, such groups will likewise be present as end groups in the intercalcated polymers.

This invention also comprises the use of the above polymers to form relief images. In this process an article comprising a layer of a photosensitive polymer of this invention generally as a film of a thickness of 0.01 to 25 mils on an inert substrate is imagewise exposed to radiation of wavelength 2000 Å to 8000 Å, preferably 2000 Å to 5000 Å, for a time sufficient to effect substantial cleavage of the polymer. The exposed article is then developed by heating at 50° to 170°, preferably in the presence of an organic or an inorganic base selected from tertiary amine, alkali metal hydroxide or alkali metal carbonate. When an organic base is employed, the preferred temperature of development is 120° C. to 160° C. With inorganic bases, the preferred temperature range is from 60° C. to 120° C. Development removes the photodegraded polymer to form a positive relief image.

DETAILED DESCRIPTION OF THE INVENTION

The present invention provides polyoxymethylene polymers containing photosensitive, but thermally stabilizing groups. It is well known that polyoxymethylenes degrade thermally and under the influence of base by chain unzippering to give formaldehyde, and that such polymers can be stabilized by end-capping, especially with acetate groups and by the interposition of groups in the body of the chain derived from ethylene glycol or propylene glycol, which blocks the progress of the unzippering degradation.

The polymers of the present invention contain such end caps and copolymerized groups which confer thermal stability, i.e. groups of the type:

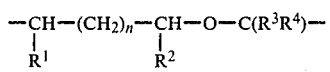

wherein both ends are joined to oxygen. At least one of $R^1$ and $R^2$ is a phenyl ring containing an orthonitro substituent, preferably o-nitrophenyl, which confers photochemical instability on the polymer. The mechanism of the photolytic reaction is not known for certain, but is believed to involve reaction of the type:

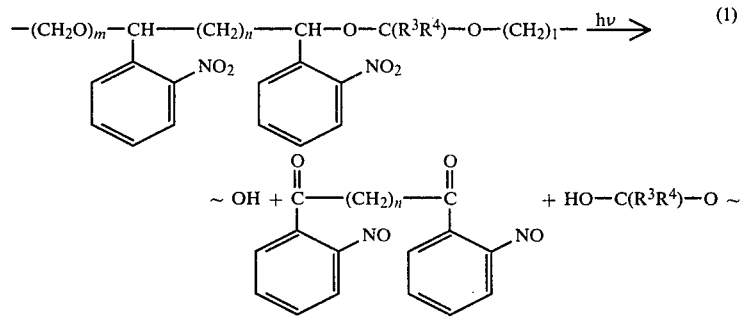

(1)

The breaks in the polymer chain thus produced provide points at which degradation can proceed by chain unzippering. Likewise end caps HOA- which contain o-nitrophenyl groups at the carbon adjoining the acetal chain can be removed photochemically to give unstable chains which can be further degraded by heating, preferably in the presence of base.

The radiation sensitive polymers of the invention are prepared by intercalation of the corresponding 1,3-dioxolanes or 1,3-dioxanes into preformed uncapped or acetate capped polyoxymethylene to obtain random incorporation of the dioxolane or dioxane units into the polymer chain. The resulting copolymer may contain dioxolane or dioxane end groups. The intercalated polymer number average molecular weight may range from ~1000–100,000 i.e. from lower molecule weight oligomers to high molecular weight polymer, depending upon the molecular weight of the polyoxymethylene starting weight.

In the intercalation process, the dioxolane or dioxane is incorporated randomly into the polymer chain. Purified solvents and an anhydrous medium should be employed to prevent chain cleavage of the polymer from protonic impurities.

Intercalation is carried out by reaction of the polyoxymethylene polymer with an excess of a suitable dioxolane or dioxane in the presence of an acid catalyst. Preferred catalysts for the process of the present invention are phosphorus pentafluoride, triethyl oxonium fluoborate and boron trifluoride. Examples of other acids or acidreacting compounds that may be used as catalysts within the scope of this invention to provide a mildly acidic reaction medium include Lewis acids usually of the Friedel-Crafts type, such as aluminum trichloride, titanium tetrachloride, boron trichloride, antimony trichloride, antimony pentachloride, antimony pentafluoride; protonic or Bronsted acids with a pKa less than 5.5 including organic acids such as hydroxyacetic, trichloroacetic and para-toluenesulfonic and inorganic acids such as sulfuric, hydrochloric and phosphoric acids and the like. The salts of strong acids (pKa less than 2.0) with weak bases may also be used. The acid catalyst should be compatible with the dioxolanes and dioxanes, i.e., should not form insoluble complexes therewith or cause decomposition. Strong acids and acids which are strong oxidizing or reducing agents are not preferred and, if used, should be used sparingly to prevent excessive degradation of the polymer by causing the reaction medium to be more than mildly acidic. Excessive degradation may also be avoided by adding these acids in such a manner that the contact time of the acid with the polymer is held at a minimum. The preferred range of concentration of acid catalyst is from 0.001–0.10 part per part of polymer. The same range is preferred for their salts with weak bases. Certain complexes of the aforementioned acid halides are operable in the present invention and may be preferred when it is desired to employ a liquid catalyst, e.g., ether complexes, the preferred ether being diethyl ether. Examples of other ethers are the dialkyl ethers, such as dimethyl ether, dibutyl ether, and dipropyl ether. The complexes of the Lewis acids with ether may be prepared by mixing the respective materials in a suitable solvent. The catalyst complex may also be prepared by adding the Lewis acid to the ether. The resultant product which is an ether complex is more easily manipulated than some of the aforementioned gases.

Intercalation can be accomplished in any compatible medium in which the polymer can be intimately contacted with the desired dioxolane or dioxane. A compatible medium should be an inert liquid hydrocarbon such as toluene, ether or an aliphatic hydrocarbon, but any material which does not react with the polymer or the dioxolane or dioxane and does not excessively deactivate the catalyst may be employed. Aliphatic hydrocarbons are preferred solvents with heptane being particularly preferred.

The time of reaction may be as long as is necessary to reach completion of the reaction without excessive decomposition of the unstabilized polymer. With long reaction times, temperatures as low as 25° C. may be employed and with short reaction times, temperatures as high as 200° C. may be employed. The temperature, time, concentration of reactants and strength of catalyst must be balanced, as in most other reactions, so as to cause an acceptable amount of reaction in a reasonable time. The chains of the polymer are susceptible to attack by acids and may be cleaved by such an attack: therefore, it is important to adjust the reaction temperature and time so that the cleavage and other side reactions that take place are slow enough and yet intercalation of the polymer is fast enough to obtain an acceptable product.

Generally, impurities which adversely affect the polymerization of anhydrous formaldehyde to high molecular weight polymers and oxygen should be avoided in this process.

In a preferred embodiment of the process, intercalation is carried out with $BF_3 \cdot (C_2H_5)_2O$ catalyst in heptane at a temperature of 70°–100° C. for a reaction time of 0.5–3 hours. Any unreacted dioxolane or dioxane may be recovered at the conclusion of the intercalation.

The intercalated polymer may possess sufficient thermal stability to be molded without further refining; however, it is desirable to neutralize the catalyst and to remove unreacted polyoxymethylene or uncapped polyoxymethylene end groups. A suitable method for such refining includes dissolving the polymer in the absence of oxygen in a solution containing an amine or caustic, and heating the solution to depolymerize unreacted polymer. Solvents which may be used in the presnce of an amine include the aliphatic and aromatic hydroxy compounds, such as cyclohexanol, ethylene glycol, benzyl alcohol and phenol. The preferred solvents for caustic treatment are benzyl alcohol or cyclohexanol. Amines and caustics which are useful in the purification step include triethylamine, tripropylamine, tributylamine, sodium hydroxide, and potassium hydroxide. Another procedure which may be employed for removing the uneacted polyoxymethylene is thermal degradation of the polymer either solid, molten or in solution without addition of an amine or a caustic after removal or deactivation of the catalyst.

Intercalation of polyoxymethylene polymers with nonphotodegradable dioxolanes is discussed in U.S. Pat. No. 3,477,994, 3,437,640 and 3,183,211.

The intercalated polymers may have a number average molecular weight between 1000 and about 100,000. The preferred polymers have an inherent viscosity, measured at 30° C. using a 0.5% solution in hexafluoroisopropanol solvent, of 0.7 to 1.5. This corresponds to a number average molecular weight of about 15,000 to about 40,000. The radiation-sensitive -A- group should be present to the extent of from 1 unit for 20 —$CH_2O$— units (especially in low molecular weight polymers) to 1 for 1000 —$CH_2O$— units, preferably 1 unit per 100–500 formaldehyde units.

The concentration of the -A- groups can be conveniently determined by ultraviolet spectroscopy using the molar extinction coefficient of the aromatic substituents, which can be obtained from the dioxane or dioxolane starting materials or their glycol antecedents. For o-nitrophenyl groups, a band at 267 nm is employed having an extinction coefficient $\epsilon = 4,500$.

Transparent films of the intercalated polymers can be obtained by melt pressing the polymer at elevated temperatures, preferably 170°–180° C., at 300–2000 psi. Precautions should be taken to prevent exposure of the polymer to air at these elevated temperatures to prevent oxidation and formation of bubbles. Additions of known antioxidants or thermal stabilizers to prevent chemical or physical decomposition during the molding operation is sometimes desirable. Films of the polymers may also be obtained by solution casting.

The novel 1,3-dioxolanes and 1,3-dioxanes required as starting materials for the intercalated polymers are prepared from the corresponding glycols by procedures well known in the art. For example, reaction of the glycol with an aldehyde or ketone in the presence of an acid catalyst, preferably in an inert solvent, readily gives the corresponding 1,3-dioxolane, or dioxane, i.e.,

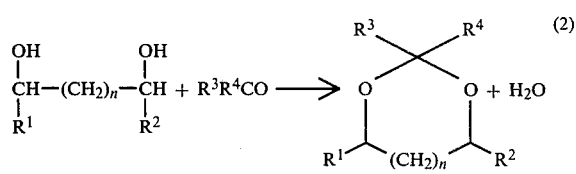

Excess aldehyde or ketone may be employed to force the reaction to completion. Alternatively, the water formed in the reaction may be removed by azeotropic distillation and the product subsequently recovered. Preferred catalysts include sulfuric acid, benzenesulfonic acid and particularly p-toluenesulfonic acid. Reaction is conveniently carried out at the reflux temperature of the solvent. Preferred solvents include aromatic hydrocarbons with benzene, toluene, and the xylenes being particularly preferred.

Alternatively, the dioxolanes and dioxanes may be prepared by an exchange reaction:

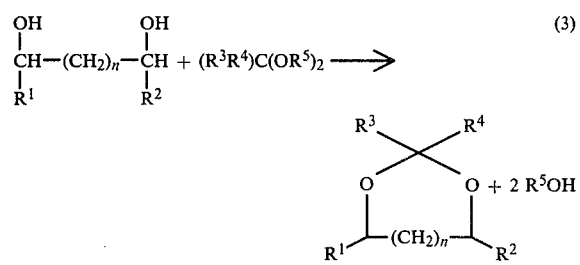

The group $R^5$ of the acetal reactant should preferably be lower alkyl. The exchange reaction is preferably carried out in the same inert solvents used in the process of equation 2, and it is also catalyzed by an acid catalyst, preferably p-toluenesulfonic acid. This exchange process is preferably used for the preparation of dioxolanes and dioxanes in which both $R^3$ and $R^4$ are H.

The 1,2-glycols are prepared by hydroxylation of the corresponding styrenes and stilbenes using conventional oxidation procedures. For example, hydroxylation may be achieved with hydrogen peroxide or potassium chlorate, catalyzed by osmium tetraoxide. Alternatively, oxidation of the olefin to the corresponding epoxide followed by alkaline or acid hydrolysis to the corresponding glycol may be employed. When potassium chlorate oxidation is employed, the reaction is preferably carried out in aqueous tetrahydrofuran solution in the presence of a catalytic amount of osmium tetraoxide. The oxidation is completed by either stirring at 25° or heating the reaction mixture under reflux for several hours. Thus hydroxylation of the known substituted styrenes and stilbenes of Column A, Table I, can give the corresponding substituted 1,2-glycols of Column B.

TABLE I

| Column A | Column B |
|---|---|
| $O_2N\text{-}C_6H_3(NO_2)\text{-}CH=CH_2$ | $O_2N\text{-}C_6H_3(NO_2)\text{-}CH(OH)CH_2OH$ |
| $O_2N\text{-}C_6H_2(NO_2)_2\text{-}CH=CH_2$ | $O_2N\text{-}C_6H_2(NO_2)_2\text{-}CH(OH)CH_2OH$ |
| $O_2N\text{-}C_6H_2(NO_2)_2\text{-}CH=CH\text{-}C_6H_2(NO_2)_3$ | $O_2N\text{-}C_6H_2(NO_2)_2\text{-}CH(OH)CH(OH)\text{-}C_6H_2(NO_2)_3$ |
| $O_2N\text{-}C_6H_3(NO_2)\text{-}CH=CH\text{-}C_6H_5$ | $O_2N\text{-}C_6H_3(NO_2)\text{-}CH(OH)CH(OH)\text{-}C_6H_5$ |
| $o\text{-}O_2N\text{-}C_6H_4\text{-}CH=CH\text{-}C_6H_4\text{-}NO_2\text{-}p$ | $o\text{-}O_2N\text{-}C_6H_4\text{-}CH(OH)CH(OH)\text{-}C_6H_4\text{-}NO_2\text{-}p$ |
| $O_2N\text{-}C_6H_2(NO_2)_2\text{-}CH=CH\text{-}C_6H_5$ | $O_2N\text{-}C_6H_2(NO_2)_2\text{-}CH(OH)CH(OH)\text{-}C_6H_5$ |
| $o\text{-}O_2N\text{-}C_6H_4\text{-}CH=CH\text{-}C_6H_4\text{-}NO_2\text{-}o$ | $o\text{-}O_2N\text{-}C_6H_4\text{-}CH(OH)CH(OH)\text{-}C_6H_4\text{-}NO_2\text{-}o$ |
| $C_6H_3(NO_2)_2\text{-}CH=CH\text{-}C_6H_5$ | $C_6H_3(NO_2)_2\text{-}CH(OH)CH(OH)\text{-}C_6H_5$ |
| $O_2N\text{-}C_6H_3(NO_2)\text{-}CH=CH\text{-}C_6H_4(CH_3)$ | $O_2N\text{-}C_6H_3(NO_2)\text{-}CH(OH)CH(OH)\text{-}C_6H_4(CH_3)$ |
| $o\text{-}O_2N\text{-}C_6H_4\text{-}CH=CH\text{-}C_6H_5$ | $o\text{-}O_2N\text{-}C_6H_4\text{-}CH(OH)CH(OH)\text{-}C_6H_5$ |
| $O_2N\text{-}C_6H_2(NO_2)_2\text{-}CH=CH\text{-}C_6H_3(NO_2)_2$ | $O_2N\text{-}C_6H_2(NO_2)_2\text{-}CH(OH)CH(OH)\text{-}C_6H_3(NO_2)_2$ |
| $O_2N\text{-}C_6H_2(NO_2)_2\text{-}CH=CH\text{-}C_6H_3(NO_2)_2$ | $O_2N\text{-}C_6H_2(NO_2)_2\text{-}CH(OH)CH(OH)\text{-}C_6H_3(NO_2)_2$ |
| $O_2N\text{-}C_6H_2(NO_2)_2\text{-}CH=CH\text{-}C_6H_4\text{-}NO_2$ | $O_2N\text{-}C_6H_2(NO_2)_2\text{-}CH(OH)CH(OH)\text{-}C_6H_4\text{-}NO_2$ |
| $O_2N\text{-}C_6H_2(NO_2)_2\text{-}CH=CH\text{-}C_6H_4\text{-}NO_2$ | $O_2N\text{-}C_6H_2(NO_2)_2\text{-}CH(OH)CH(OH)\text{-}C_6H_4\text{-}NO_2$ |

TABLE I-continued
| Column A | Column B |
|---|---|
| 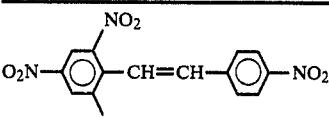 | 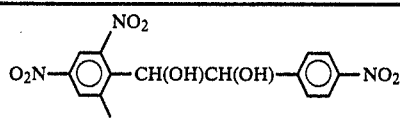 |
| 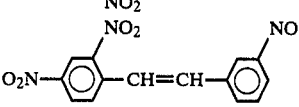 | 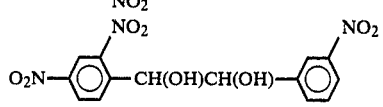 |
| 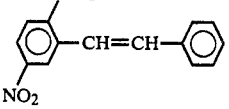 | 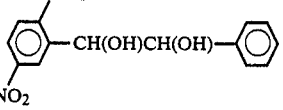 |
| 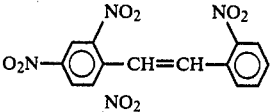 | 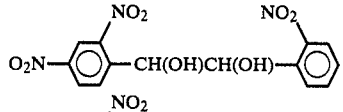 |
| 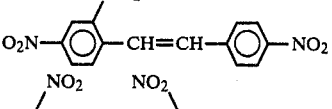 | 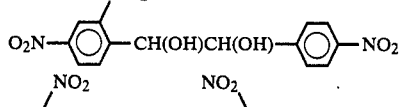 |
| 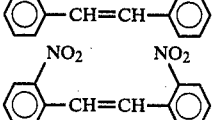 | 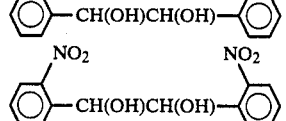 |
| 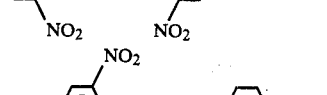 | 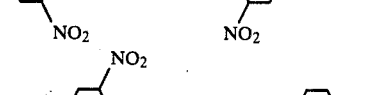 |
| 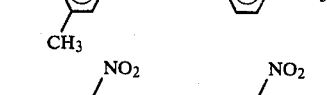 | 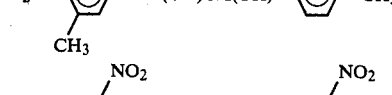 |
| 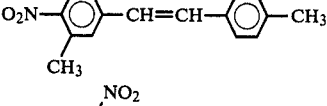 | 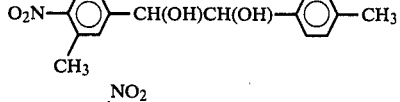 |
| 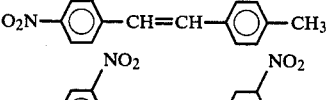 | 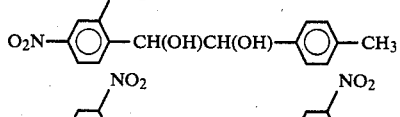 |
| 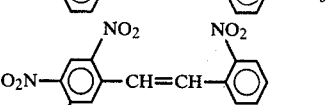 | 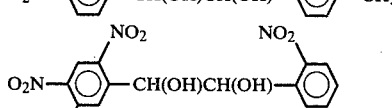 |
| 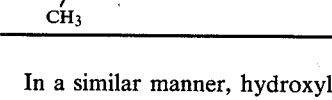 | 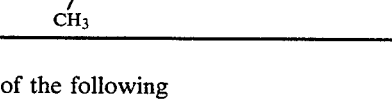 |
In a similar manner, hydroxylation of the following substituted styrenes and stilbenes will give the corresponding substituted glycols.
| Column A | Column B |
|---|---|
| 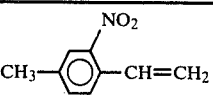 | 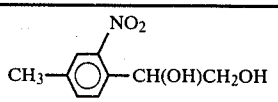 |
| 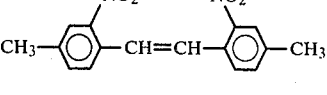 | 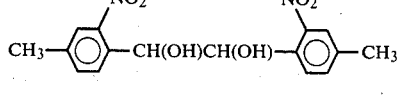 |

| Column A | Column B |
|---|---|

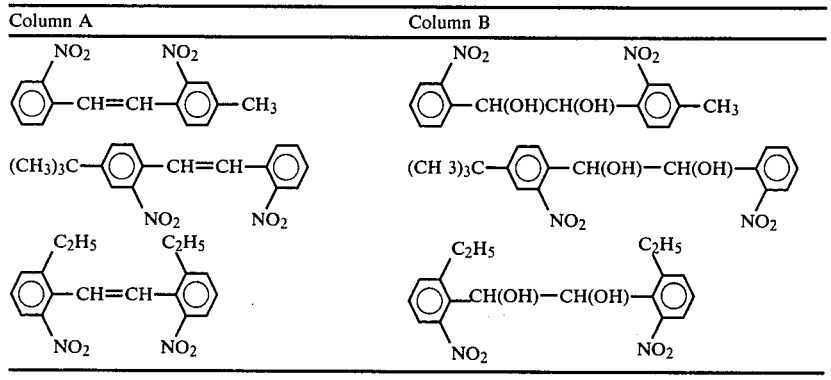

1-(o-Nitrophenyl)-1,3-dihydroxypropane can be made by the reaction of o-nitrobenzaldehyde with ethyl bromoacetate followed by lithium aluminum hydride reduction, cf. Schaal, Bull. Soc. Chem., part 2, 11 3083 (1973) for preparation of the isomeric 1-(m-nitrophenyl)-1,3-dihydroxypropane.

Preparation of the dioxane of 1-(o-nitrophenyl)-1,3-dihydroxypropane can also be made by the Prins reaction of o-nitrostyrene with formaldehyde and dilute sulfuric acid., cf. Coussemant et. al., Bull. Soc. Chim. Fr., (12), 4355 (1970); ibid., (3) 877 (1971), showing the preparation of the dioxane of 1-(m-nitrophenyl)-1,3-dihydroxypropane by this method.

1,3-Di(o-nitrophenyl)-1,3-dihydroxypropane can be prepared by forming vinyl o-nitrobenzoate by ester exchange of vinyl acetate with o-nitrobenzoic acid. Self-condensation of vinyl o-nitrobenzoate in the presence of aluminum chloride gives 1,3-di(o-nitrophenyl)-propane-1,3-dione which can be reduced with lithium aluminum hydride to the desired 1,3-diol. Cf. Rao and Filler, J. Org. Chem., 36, 1447 (1971), disclosing the self-condensation of vinyl p-nitrobenzoate.

In this specification and claims the term "lower alkyl" refers to an alkyl group of 1 to 4 carbon atoms.

The imaging process of this invention may employ suitable sheet material having a radiation sensitive coating on one surface thereof. This sheet material is formed by coating or impregnating a suitable substrate with the radiation sensitive copolymer following known techniques. By "substrate" is meant any natural or synthetic support which is capable of existing in film or sheet form and can be flexible or rigid. For example, the substrate could be a metal sheet or foil, a sheet or film of synthetic organic resin, cellulose paper, fiberboard, and the like, or a composite of two or more of these materials. Specific substrates include alumina-blasted aluminum, alumina-blasted polyester film, polyester film, polyvinyl alcohol-coated paper, crosslinked polyester-coated paper, nylon, glass, heavy paper such lithographic paper, and the like.

When the copolymer compositions are coated on metal surfaces, they are useful for making lithographhic printing plates. For example, use of a grained aluminum base in combination with a radiation sensitive copolymer results in a developed lithographic plate. The plate, after radiation and image development, is first coated with an aqueous solution of Age (Pitman Co.) and is then contacted with a roller which wets only the photopolymer image with ink. The inked plate can then be used in lithographic printing in the usual way.

The photodegradable copolymer compositions may optionally contain other materials inert to the photodepolymerization reaction. Such materials include thermoplastic and nonthermoplastic binders useful for varying the physical properties of the resultant polymeric images. In addition, plasticizers may be added to lower the glass transition temperature and facilitate selective stripping. If desired the polymers may also contain immiscible polymeric or nonpolymeric organic or inorganic fillers or reinforcing agents which are essentially transparent, e.g., the organophilic silicas, bentonites, silica, powdered glass, colloidal carbon, as well as various types of dyes and pigments. Other useful additives which may be employed include sesitizers to improve the efficiency of the radiation and adhesion promoters.

The radiation sensitive copolymer, as a solution in a carrier solvent, may be sprayed, brushed, applied by a roller or an immersion coater, flowed over the surface, picked up by immersion or applied to the substrate by other means. The solvent is then allowed to evaporate. Useful solvents include those known in the art to dissolve polyoxymethylene, e.g., hexafluoroisopropanol, phenol and substituted phenols including the halophenols, nitrophenols and cresols, benzyl alcohol and other fluorinated alcohols such as $\alpha,\alpha$-di(trifluoromethyl)benzyl alcohol. Coating temperatures range from about 0°–150° C. depending upon the solvent employed. Alternatively, substrate coating may be achieved by hot-pressing a film of the copolymer to the substrate or by melt-coating techniques.

The radiation sensitive copolymers are exposed to radiation of wavelength in the 2000–8000Å range, preferably 2000–5000Å. Suitable sources of such light, in addition to sunlight, include carbon arcs, mercury-vapor arcs, fluorescent lamps with ultraviolet radiation-emitting phosphors, electronic flash units, and photographic flood lamps.

Where artifical radiation sources are used, the distance between the photosensitive layer and the radiation source may be varied according to the radiation sensitivity of the copolymer. Customarily, mercury-vapor arcs are used at a distance of 1.5 to 20 inches from the photosensitive layer.

Imagewise exposure, for example, in preparing printing plates, is conveniently carried out by exposing a layer of the photoactive copolymer to radiation through a process transparency; that is, an image-bearing transparency consisting solely of areas substantially opaque and substantially transparent to the radiation being used where the opaque areas are substantially of the same optical density, for example, a so-called line or halftone negative or positive. Variable depth images may also be obtained by exposure through a continuous tone transparency. Process transparencies may be constructed of any suitable materials including cellulose acetate film and oriented polyester film.

The length of time for which the compositions are exposed to radiation may vary upwards from a few seconds. Exposure times will vary, in part, according to the nature of the copolymer and the concentration and types of o-nitrophenyl moieties present, and the type of radiation.

Image development is accomplished by depolymerization of the unstable polymer chains formed in the irradiated areas of the copolymer composition. The depolymerizations, which can be assisted by basic materials, are carried out at temperatures 25°-170° C. for times of a few minutes to several hours. The basic materials can be organic amines such as tributyl amine or inorganic bases such as potassium hydroxide, sodium hydroxide, or sodium carbonate dissolved in water, organic solvents, such as methanol, ethanol, propanol, iospropanol, butyl alcohols, benzyl alcohols, tetrahydrofuran, and dioxane, or in aqueous-organic mixtures thereof. When a basic material is not used, heating the composition at 120°-160° C. is preferred,. When a basic organic material is used for more rapid development, the preferred method is to apply to the composition enough tributylamine to totally cover the surface and to heat the composition at 120°-160° C. When an inorganic basic solution is employed, lower development temperatures may be used, and the preferred method is to use 0.1%-20% potassium hydroxide in isopropanol at 68°-100° C. After development, there results a positive image, i.e., polymer remains under the opaque areas of the process transparency, that is the areas not struck by radiation passing through the transparency.

EMBODIMENTS OF THE INVENTION

This invention is further illustrated by the following specific embodiments, which should not, however, be construed as fully delineating the scope of this discovery.

Care was taken to exclude moisture during the intercalation procedures for the preparation of polymers. All apparatus for intercalation runs was dried in a vacuum over for several hours prior to the experiments and material transfers were done under a nitrogen atmosphere.

Example 1 o-Nitrophenylethylene Glycol o-Nitrostyrene (42.15 g, 0.28 mole) in 300 ml of tetrahydrofuran (THF) was added to a suspension of 43.0 g of potassium chlorate (0.35 mole) in 300 ml of water. Osmium tetroxide (0.25 g) in 25 ml of THF was added to give immediately the brown color of osmate ester. The reaction mixture was heated at reflux for 48 hrs. under nitrogen with efficient stirring. The layers were separated and the lower, predominantly aqueous, layer was saturated with sodium chloride and extracted twice with 450 ml of THF. The THF extracts and original upper layer were combined, dried, and concentrated in vacuo to give 58 g of dark oil. This material was chromatographed on a silicic acid column (325 g). Elution with hexane and 25% ether-hexane gave small amounts of the desired glycol and further elution with 50% etherhexane gave 20 g of crystalline crude glycol. The product was purified by washing with ether to give 14.5 g of pure glycol. Rechromatography of the other fractions and ether washing gave an additional 5.0 g of glycol for a total yield of 19.5 g of o-nitrophenylethylene glycol. Recrystallization of the product from THF-hexane gave pale yellow crystals, mp 95°-96°.

ir(Nujol): ($\mu$) 3.0–3.1, 6.55, 7.50, 9.4–9.5, 9.82, 11.03, 11.70, 12.05, 12.65, 13.50.

Hnmr (DMSO-$d_6$): ($\delta$) 7.40-7.96 (4H, mult., arom.); 5.57 (2H, doub. CHO$\underline{H}$); 5.18 (1H, quart., C$\underline{H}$OH); 4.83 (1H, trip., CH$_2$O$\underline{H}$); 3.53 (2H, trip., C$\underline{H}_2$OH).

UV(CH$_3$OH): (nm $\lambda_{max}$ 345 ($\epsilon$403); $\lambda_{max}$ 257 ($\epsilon$4410).

Anal. Calcd for $C_8H_9NO_4$: C, 52,46; H, 4.95; N, 7.65; Found: C, 52.30; H, 4.73; N, 7.51.

Example 2

1,2-Di-o-Nitrophenylethylene Glycol o,o'-Dinitrostilbene, the starting material for 1,2-di-o-nitrophenylethylene glycol, was prepared by the following procedure: addition of 50 ml of 58% HI to 10.0 g of trans-(o,o'-dinitro)stilbene oxide resulted in a mildly exothermic reaction, and the reaction mixture became partially homogeneous with concomitant iodine color formation. After being stirred at 25° for 17 hr., the reaction mixture was filtered to leave a gummy solid. This material was washed with water and with saturated sodium bisulfite solution, and it was triturated with ether to leave 5.03 g (54%) of o,o'-dinitrostilbene, mp 195°-197° C. When shorter reaction times were used or when the reaction was cooled in ice during the addition of HI, the corresponding iodohydrin was isolated.

o,o'-Dinitrostilbene (9.2 g) in 270 ml of THF was added to a suspension of 9.0 g of potassium chlorate in 150 ml of water. Osmium textroxide (0.25 g) in 25 ml of THF was added, and the reaction mixture was heated at reflux for 48 hrs. under nitrogen with efficient stirring. The layers were separated and the lower, predominantly aqueous, layer was saturated with sodium chloride and extracted with THF. The THF extracts and original upper layer were combined, dried, and concentrated in vacuo to give 8.35 g of dark oil. This material was chromatographed on a silicic acid column. Elution with 20% ether-hexane gave o-nitrobenzaldehyde, and further elution with 50% ether-hexane gave 4.22 g of crystalline glycol. Recrystallization from THF-hexane gave pure 1,2-di-o-nitrophenylethylene glycol, mp 129°-131°C.

ir (Nujol): ($\mu$) 2.90-3.00, 6.55, 7.43, 8.42, 9.50, 9.70, 11.63, 12.70, 13.32, 14.15.

Hnmr(DMSO-$d_6$): ($\delta$) 7.0-7.9 (8H, mult.,arom.); 5.90 (2H, doub., OH); 5.60 (2H, doub., CH).

Anal. Calcd for $C_{14}H_{12}N_2O_6$: C, 55.26, H, 3.98; N, 9.21

Found: C, 55.29; H, 4.06; N, 9.22.

Example 3

4-o-Nitrophenyl-1,3-dioxolane o-Nitrophenylethylene glycol (46.0 g, 0.25 mole), diethoxymethane (28.0 g, 0.27 mole), and 10 p-toluenesulfonic acid in 300 ml benzene were heated under reflux under nitrogen for 7 hrs. The reaction mixture was diluted with 200 ml of benzene and extracted three times with 5% aqeous sodium hydroxide solution, and dried. The solution was concentrated in vacuo to give 39.7 g of yellow liquid. The product was purified by distillation to give 38.4 g of pure 4-o-nitrophenyl-1,3-dioxolane, bp 85° (0.15 mm), $n_D^{25}$ 1.5562.

ir(neat): (μ) 6.55, 7.50, 8.68, 9.23, 10.55, 10.70, 11.70, 12.65, 13.50, 13.90.

Hnmr(CDCl$_3$): (δ) 7.25–8.17 (4H, mult., arom.); 5.50 (1H, CH); 5.28 (1H, sing., OCH$_2$O); 5.00 (1H, sing., OCH$_2$O); 4.42 (1H, trip., CH$_2$); 3.70 (1H, CH$_2$).

UV(CH$_3$OH): (nm) λ$_{max}$ 345 (369); λ$_{max}$ 260 (5870).

Anal. Calcd. for C$_9$H$_9$NO$_4$: C, 55.39; H, 4.65; N, 7.18; Found: C, 55.27; H, 4.73; N, 7.23.

Example 4

2,2-Dimethyl-4-o-nitrophenyl-1,3-dioxolane

A solution of o-nitrophenylethylene glycol (31.25 g, 0.17 mole) and 2 g of p-toluenesulfonic acid in 120 ml of acetone was heated under reflux under nitrogen for 15 hrs. The reaction mixture was diluted with benzene, extracted twice with 5% aqueous sodium hydroxide solution, and dried. The solution was concentrated in vacuo to give 17.9 g of yellow liquid. The product was purified by distillation to give 14.6 g of pure 2,2-dimethyl-4-o-nitrophenyl-1,3-dioxolane, bp 93° (0.2 mm), n$_D^{24}$ 1.5292.

ir (neat): (μ) 6.55, 7.30, 7.45, 8.2–8.3, 8.65, 9.45, 11.60, 11.80, 12.65, 13.45.

Hnmr(CDCl$_3$): (δ) 7.2–8.1 (4H, mult., arom.); 5.57 (1H, trip., CH); 4.60 (1H, trip., CH$_2$); 3.70 (1H, CH$_2$); 1.50 (6H, doub., CH$_3$).

UV(CH$_3$OH); (nm) λ$_{max}$ 345 (390); λ$_{max}$ 260 (5420).

Anal. Calcd for C$_{11}$H$_{13}$NO$_4$: C, 59.19; H, 5.87; N, 6.27. Found: C, 59.01; H, 5.94; N, 6.29.

Example 5

4,5-Di-o-nitrophenyl-1,3-dioxolane

A solution of 4.5 g of 1,2-di-o-nitrophenylethylene glycol, 2.0 g of diethoxymethane, and 2.0 g of p-toluenesulfonic acid in 30 ml benzene was heated under reflux under nitrogen for 15 hrs. The reaction mixture was diluted with ether, extracted with 5% aqueous sodium hydroxide solution, and dried. The solution was concentrated in vacuo to give 4.42 g of gummy solid. Recrystallization from THF-hexane gave 3.7 g of pale yellow 4,5-di-o-nitrophenyl-1,3-dioxolane, mp 137°–139°.

ir(Nujol): (μ) 6.55, 7.40, 7.50, 8.70, 9.15, 9.75, 10.50, 10.70, 11.60, 11.68, 12.50, 12.60, 13.30, 13.45, 13.65.

Hnmr(DMSO-d$_6$): (δ) 7.5–8.2 (8H, mult., arom.); 5.70 (2H, sing., CHAr); 5.05 (2H, sing., CH$_2$). Anal. Calcd for C$_{15}$H$_{12}$N$_2$O$_6$: C, 56.96; H, 3.82; N, 8.86. Found: C, 57.16; H, 4.00; N, 8.94.

Example 6

Preparation of Photosensitive Polyoxymethylene Polymer

Uncapped polyoxymethylene (10.00 g, MW 25,000–30,000) was dried in vacuo in a 100 ml 2-necked flask at 100° C. for 1 hr. The center neck had a stopcock adaptor to a vacuum pump, and the side arm was fitted with a serum cap. The weight of dried polymer was 9.47 g (5.3% loss). A nitrogen bubbler was substituted for the vacuum pump and 30 ml of heptane (freshly distilled from calcium hydride) and 2.0 ml of freshly distilled 4-o-nitrophenyl-1,3-dioxolane were added via syringe through the serum cap under nitrogen. The nitrogen bubbler valve was closed, and the reaction mixture was immersed in a preheated 75° bath for 15 mins. with magnetic stirring. After the addition of 0.05 ml of fresh BF$_3$·(C$_2$H$_5$)$_2$O the slurry was maintained at 70°–75° for 1 hr. The reaction was quenched with 5 ml of tributylamine, and the product was cooled, filtered, and washed thoroughly with methanol and acetone. The weight of dried, light sensitive, intercalated polymer, obtained as a colorless or very pale yellow solid, was 9.97 g.

To improve its thermal and base stability, the polymer was post-treated by suspension in 150 ml of benzyl alcohol and 10 ml of tributylamine followed by a 30 minute nitrogen purge. The polymer was dissolved by heating the suspension rapidly to 160° and the clear yellow solution was further heated at 160° for 30 minutes followed by rapid cooling with an ice bath. The swelled and voluminous reprecipitated polymer was filtered, washed extensively with methanol and acetone and dried in vacuo at 70°. The weight of purified polymer was 4.63 g, η$_{inh}$ =0.59 (30° C., 0.5% in hexafluoroisopropyl alcohol (HFIP), MW ~15,000. Ultraviolet analysis (HFIP) showed the presence of 113 formaldehyde units/oxyethylene unit.

When uncapped polyoxymethylene polymer of molecular weight ~60,000 was intercalated as described, 9.97 g of intercalated polymer was obtained. After posttreatment as described, 4.15 g of polymer remained, η$_{inh}$ =0.63 (30° C., 0.5% in HFIP). Ultraviolet analysis showed the presence of 117–128 formaldehyde units/oxyethylene unit.

Unsupported flexible, transparent films, 2 mils in thickness, were pressed from the purified polymer at 175°, 500 psig for 30 seconds. Use of an aluminum panel gave a film supported on the panel. Use of higher pressures, i.e. 20,000 psi, for 1 minute gave thin (<0.5 mil) films.

Example 7

Preparation of Photosensitive Polyoxymethylene Polymer

Acetate-capped polyoxymethylene (10.00 g, MW ~60,000) was intercalated with 2.0 ml of 4-o-nitrophenyl-1,3-dioxolane using the procedure described in Example 6. The weight of dried, light sensitive, intercalated polymer, obtained as a colorless or very pale yellow solid, was 9.85 g. The polymer was post-treated as described to give 6.64 g of thermal and base-stable polymer, η$_{inh}$ =0.97 (30° C., 0.5% in HFIP), MW ~25,000. Ultraviolet analysis (HFIP) showed the presence of 200–250 formaldehyde units/oxyethylene unit.

Example 8

The intercalation experiment described in Example 7 was repeated on a larger scale with 110.0 g of acetate-capped polyoxymethylene (MW ~60,000) and 23 ml of 4-o-nitrophenyl-1,3-dioxolane in 240 ml of heptane in a 500-ml flask. Reaction was initiated with 0.5 ml of BF$_3$·(C$_2$H$_5$)$_2$O and it was quenched with 10 ml of tributylamine. The weight of dried, light sensitive, intercalated polymer was 110.3 g. The polymer was post-treated as described in Example 6 (600 ml of benzyl alcohol and 30 ml of tributylamine were used; nitrogen purge of 2 hrs.) to give 61.2 g of stabilized polymer, η$_{inh}$ =0.72 (30° C., 0.5% in HFIP), MW ~18,000.

Example 9

4,5-Di(o-nitrophenyl)-1,3-dioxolane Intercalant

Acetate capped polyoxymethylene (7.00 g, MW ~60,000) was dried in vacuo in a 50 ml three-neck flask at 100°–105° for 1 hr. As the flask was allowed to cool to 70°, the internal pressure was raised to one atmosphere with dry nitrogen gas. To the flask was added 21.0 ml heptane (freshly distilled from CaH$_2$) and 2.29 g of 4,5-di(o-nitrophenyl)-1,3-dioxolane. The reaction mixture was stirred well and then immersed in an oil bath preheated to 75°. When the reaction mixture temperature reached 66°, there was added 0.005 ml BF$_3$.Et$_2$O. After the mixture was stirred 30 mins. at 66°–68°, an additional 0.005 ml BF$_3$.Et$_2$O was added. After the mixture was stirred a further 30 mins. at 68°–69°, the reaction was quenched by adding 1.0 ml tri-n-butylamine. The solid polymer was collected on a filter and washed thoroughly, first with methanol and finally with acetone. There was obtained 6.37 g of dry white solid intercalated polymer. $\eta_{inh}$ 0.88 (30° C., 0.5% in HFIP), MW~21,000. Ultraviolet analysis (HFIP) showed the presence of 2890 formaldehyde units/oxyethylene unit.

Example 10

2,2-Dimethyl-4-(o-nitrophenyl)-1,3-dioxolane Intercalant

Acetate capped polyoxymethylene (7.00 g, MW ~60,000) was dried in vacuo in a 50 ml three-neck flask at 100°–105° for 1 hr. As the flask was allowed to cool to 70°, the internal pressure was raised to one atmosphere with dry nitrogen gas. To the flask was added 21.0 ml of heptane (freshly distilled from CaH$_2$) and 3.00 ml of 2,2-dimethyl-4-(o-nitrophenyl)-1,3-dioxolane. The reaction mixture was stirred at 73°–78° for 15 mins., then 0.005 ml BF$_3$.Et$_2$O was added and the reaction mixture was stirred an additional 30 mins. at 75°–78°. A second portion of 0.005 ml BF$_3$.Et$_2$O was added followed by an additional 30 mins. of stirring at 75°. The reaction was quenched by addition of 1.0 ml tri-n-butylamine. The solid polymer was collected on a filter and washed thoroughly with 2-propanol, methanol and finally acetone. There was obtained 6.20 g of dry white solid intercalated polymer, $\eta_{inh}$ 1.21 (30° C., 0.5% in HFIP), MW~33,000. Ultraviolet analysis (HFIP) showed the presence of 167 formadehyde units/oxyethylene unit.

Example 11

A 0.5 mil thick film of an intercalated polyoxymethylene polymer, prepared as described in Example 6, was pressed into an aluminum panel. The film was exposed through a process transparency held in place with a vacuum frame to provide good contact of the transparency with the film, to radiation from a 275 W sunlamp at a distance of 12 inches for 5 minutes. No visible latent image was observed. The plate was placed in a 140° oven; after 3 minutes an image was clearly visible in the areas of the film not struck by radiation. Heating was continued for 1.5 hours, and a positive relief image with good resolution was obtained.

Optionally, the use of an amine, e.g. tributylamine, may be employed to increase the rate of image development.

Example 12

Preparation of a Positive Lithographic Printing Plate

A 0.25–0.50 mil thick film of an intercalated polyoxymethylene polymer, prepared as described in Example 6, was pressed into a grained aluminum panel. The film was exposed through a process transparency as described in Example 11. The exposed film was treated with tributylamine, and the plate was heated at 120°–156° for 2.5 hours. A positive relief image was observed after 19 minutes of development, and the further heating caused little further visible change. The plate was immersed in an HFIP bath for a few seconds to dissolve a small amount of organic "scum" present in the radiation-struck areas, and the plate was quickly flushed with water to leave a hydrophilic aluminum surface in the exposed areas and residual oleophilic polymer in the non-radiation struck areas. The plate was treated with gum arabic, inked and the inked plate used to print the transparency image on paper.

Example 13

A thin (~0.5 mil) film, prepared by hot pressing the intercalated polymer of Example 9, was irradiated through a process transparency with a 275 watt sunlamp for 10 minutes at a distance of six inches. The irradiated film was developed by heating in air at 160° for 20 minutes. A good positive image with deep relief was obtained.

This experiment was repeated with the intercalated polymer of Example 10. After image development for 30 minutes at 160°, an excellent positive image with deep relief was obtained.

Example 14

A 5.7% solution of the intercalated polyoxymethylene polymer of Example 6, in hexafluoroisopropanol, was bar-coated onto a grained aluminum panel to yield an air-dried coating weight of 0.05 g/dm$^2$. The coated plate was next heated (one hour) at 125°–170° C. to improve adhesion, then exposed through a positive litho film. The positive transparency was positioned over the photosensitive coating and held in intimate contact with a 6.5-mm thick glass plate. The plate was exposed for 15 minutes to a fluorescent source producing 1.9 mj/cm$^2$ of radiant energy between 300–420 nm at the plane of the coated plate (ca. 2 cm. from the ultraviolet lamps). The exposed plate, minus transparency and glass plate, was next immersed in isopropanol saturated with potassium hydroxide for 5 minutes at room temperature. This development step left a positive image since the radiation-struck areas were soluble in the alcoholic-potassium hydroxide solution. After rinsing with water, the plate was used to print the positive litho film image on paper as described in Example 12.

Example 15

Results substantially equivalent to Examples 12 and 14 were obtained when repeated with the following changes:
 (a) Grained aluminum was spin-coated using a solution containing the polymer of Example 6 (4.5 g) in a mixture of hexafluoroisopropanol (60 ml)/α,α-di-(trifluoromethyl) benzyl alcohol (60 ml); air-drying left a coating <0.0025 mm thick, a coating weight of ca. 0.2 mg/cm$^2$.
 (b) The photosensitive layer was imagewise exposed (5 minutes) in a commercial nuArc® vacuum frame (Model FT 26L) containing a 2000-watt Xenon source, 43.2 cm. from the sample.
 (c) The image was developed by immersion (5 minutes) in basic isopropanol (2% KOH) maintained at 70° C.

The following two examples illustrate image formation resulting from the formaldehyde generated in the irradiated areas.

Example 16

The polymer of Example 6 (0.6 g), dissolved in hexafluoroisopropanol (10 ml), was brush-coated onto biaxially oriented polyethylene terephthalate film (0.127 mm-thick); air drying left a very thin (<0.0025 mm), transparent, photosensitive layer. The photosensitive layer was then overcoated with polyvinyl alcohol (1 g), (viscosity 28-32 Cp., 4% aqueous solution, 20° C., Heoppler falling ball) dissolved in water (20 ml) using a doctor blade with a clearance of 0.127 mm. After drying at 120° C., the sample was imagewise exposed (6 minutes) to the nuArc® source described in Example 15. A vesicular image was then obtained in the thermoplastic polyvinyl alcohol layer on brief (<1 minute) heating to 240° C. The formaldehyde, released imagewise, produced bubbles in the exposed areas.

Example 17

A relatively thick coating (ca. 0.038 mm) of the polymer of Example 6 was applied onto a glass microscope slide. The photosensitive layer was then imagewise exposed (5 minutes) through a transparency, bearing an electrical circuit design, using the ultraviolet source described in Example 14. The resulting latent image was developed by treating the surface with Tollens' reagent (an ammoniacal solution of silver hydroxide), which is a test reagent for (oxidizing) aldehydes. That is, the exposed areas, which contain formaldehyde or aldehyde-containing polymer fragments, reduce silver ion to metallic silver, which precipitates onto the irradiated areas. The thin, finely-divided, black, metallic, image precipitated is readily visible against the colorless to pale-yellow background of the unexposed areas.

The silvered, electrical circuit image was immersed (30 minutes) in a conventional electroless copper plating bath at room temperature. Upon removal from the bath and rinsing with water, a copper-plated circuit replica was obtained. The initially precipitated metallic silver catalyzed electroless copper deposition.

Example 18

Preparation of a Gravure Printing Plate

The photosensitive polymers of this invention can be photodepolymerized to yield a gravure cell relief pattern on the polymer surface. A film of the intercalated polymer of Example 6, ~0.07 mm thick, was pressed onto a grained aluminum plate. The film was imaged in a vacuum frame with a 275 W sunlamp at 15.2 cm for 10 minutes through a 30 step gray scale and a 175 line negative gravure screen. After exposure the imaged film was developed with a solution of 2% KOH in i-propyl alcohol at 70° for 45 minutes. The plates were inked with a black publication ink let down with hydrocarbon solvent (25% aromatic, 75% saturated), hand doctored with a steel blade, and hand printed by rolling immediately with a paper-covered rubber roller. The first seven steps hand printed and the depth of the first 21 steps were determined. The results demonstrate a potentially useful continuous tone response for conventional gravure.

| Step | Optical Density | Cell Depth (μ) |
|---|---|---|
| 1 | .06 | 26.7 |
| 2 | .15 | 22.9 |
| 3 | .25 | 16.5 |
| 4 | .32 | 13.3 |
| 5 | .43 | 9.52 |
| 6 | .53 | 6.98 |
| 7 | .63 | 4.83 |
| 8 | .75 | 2.79 |
| 9 | .84 | 2.06 |
| 10 | .92 | 1.53 |
| 11 | 1.02 | 1.09 |
| 12 | 1.12 | 1.02 |
| 13 | 1.19 | 0.76 |
| 14 | 1.29 | 0.69 |
| 15 | 1.38 | 0.46 |
| 16 | 1.49 | 0.38 |
| 17 | 1.59 | 0.26 |
| 18 | 1.72 | 0.25 |
| 19 | 1.82 | 0.15 |
| 20 | 1.92 | 0.13 |
| 21 | 2.00 | 0.05 |

What is claimed is:

1. A compound having the formula:

wherein $R^1$ and $R^2$ are H or phenyl substituted with up to 5 substituents of lower alkyl or nitro, with the proviso that at least one of $R^1$ and $R^2$ is a phenyl group with an orthonitro substituent.

2. The compound of claim 1 wherein $R^1$ is o-nitrophenyl and $R^2$ is H.

3. The compound of claim 1 wherein $R^1$ and $R^2$ are each o-nitrophenyl.